US006682762B2

(12) United States Patent
Register

(10) Patent No.: US 6,682,762 B2
(45) Date of Patent: Jan. 27, 2004

(54) POULTRY AND LIVESTOCK FEED ADDITIVE

(75) Inventor: Martin Kenneth Register, Montgomery, AL (US)

(73) Assignee: Heart-O-Dixie Animal Nutrition, LLC, Montgomery, AL (US)

( * ) Notice: Subject to any disclaimer, the term of this patent is extended or adjusted under 35 U.S.C. 154(b) by 0 days.

(21) Appl. No.: 09/971,669

(22) Filed: Oct. 9, 2001

(65) Prior Publication Data

US 2003/0068359 A1 Apr. 10, 2003

(51) Int. Cl.$^7$ .................. A61K 35/78; A61K 33/14; A61K 33/10; A23K 1/00; A23L 1/20
(52) U.S. Cl. .................. 424/757; 424/442; 424/678; 424/679; 424/680; 424/687; 424/696; 424/715; 424/776; 426/2; 426/623; 426/630
(58) Field of Search .................. 424/757, 442, 424/776, 678, 679, 680, 687, 696, 715; 426/2, 623, 630, 648

(56) References Cited

U.S. PATENT DOCUMENTS

| | | | |
|---|---|---|---|
| 1,645,703 A | | 10/1927 | Lapp |
| 2,683,664 A | | 7/1954 | Greer |
| 4,182,755 A | | 1/1980 | McNeff |
| 4,287,220 A | * | 9/1981 | Pappas et al. |
| 4,452,779 A | | 6/1984 | Cockerill |
| 4,540,577 A | | 9/1985 | Hunt et al. |
| 4,560,561 A | | 12/1985 | Henderson et al. |
| 4,608,257 A | | 8/1986 | Teeter |
| 4,729,894 A | | 3/1988 | Teeter |
| 4,857,332 A | | 8/1989 | Schricker |
| 4,883,907 A | * | 11/1989 | Ratz Nee Simonek et al. |
| 4,976,963 A | | 12/1990 | Schricker et al. |
| 5,252,346 A | | 10/1993 | Krause |
| 5,264,227 A | | 11/1993 | Laroche et al. |
| 5,385,735 A | * | 1/1995 | Grizzunti et al. |
| 5,863,572 A | | 1/1999 | Iwasaki et al. |
| 5,976,580 A | | 11/1999 | Ivey et al. |
| 6,103,276 A | * | 8/2000 | Pilgrim et al. |
| 6,130,250 A | * | 10/2000 | Burch et al. |
| 6,248,374 B1 | * | 6/2001 | Murray et al. |
| 6,261,609 B1 | | 7/2001 | Cates, II |

FOREIGN PATENT DOCUMENTS

| | | | |
|---|---|---|---|
| CA | 1328371 | | 4/1994 |
| CA | 2269397 | | 10/1999 |
| EP | 0 616 777 A2 | | 9/1994 |
| GB | 280774 | | 11/1927 |
| GB | 711349 | | 6/1954 |
| GB | 1330209 | | 9/1973 |
| GB | 266652 A | | 11/1993 |
| WO | WO 91/03167 | * | 3/1991 |

* cited by examiner

Primary Examiner—Christopher R. Tate
(74) Attorney, Agent, or Firm—Richard C. Litman

(57) ABSTRACT

A poultry and livestock feed additive composition containing 36 wt. % electrolytes, roughage and mineral oil to increase their dietary electrolyte balance. Addition of the electrolyte additive composition improves breeder hen performance as to egg production, body weight, and reduced mortality from heat stress. Broiler chickens on this diet result in increased processing yield, feed conversion and body weight. A method of preparing this dietary electrolyte feed for poultry and livestock is also described.

4 Claims, No Drawings

POULTRY AND LIVESTOCK FEED ADDITIVE

BACKGROUND OF THE INVENTION

1. Field of the Invention

The present invention relates generally to animal feed additives. More specifically, the invention is a fowl and livestock feed additive containing an appropriate amount of a dietary electrolyte balance additive powder containing 36% by weight electrolyte along with roughage products and mineral oil.

2. Description of the Related Art

The related art of interest describes various poultry and livestock additives, but none discloses the present invention. There is a need for an animal feed additive which is economical and effective for supplying a proper electrolytic balance for poultry and livestock.

The related art will be discussed in the order of perceived relevance to the present invention.

U.S. Pat. No. 4,608,257 issued on Aug. 26, 1986, and U.S. Pat. No. 4,729,894 issued on Mar. 8, 1988, to Robert G. Teeter describe a poultry feedstuff and drinking water additive for treating heat stress by reducing respiratory alkalosis and enhancing weight gain comprising 0.3 to 3 wt. % ammonium chloride or hydrochloric acid to provide hydrogen ions and 0.5 wt. % sodium bicarbonate in 100 parts of feed containing 48% ground corn grain, 35% of a 44% soybean meal, 6.0% corn oil, 5% meat and bone meal, 1.0% dicalcium phosphate, 0.9% calcium carbonate, 0.5% vitamin mix, 0.3% sodium chloride, 0.2% DL-methionine, 0.1% mineral, and 3.1% ground polyethylene. The feed additive and total feed composition are distinguishable for containing ammonium chloride or hydrochloric acid along with a vitamin mix.

U.S. Pat. No. 5,264,227 issued on Nov. 23, 1993, to Jean-Luc Laroche et al. describes a buffer block containing feed supplement for dairy cattle comprising at least 60 wt. % sodium bicarbonate, sodium carbonate and/or sodium sesquicarbonate, at least 20 wt. % magnesium oxide, and less than 16 wt. % molasses. Optionally, 0–10 wt. % wheat middlings, 0–5 wt. % calcium carbonate, 0–5 wt. % magnesium sulfate, 0–5 wt. % potassium sulfate, 0–0.10% vanilla flavor, 0–0.20 wt. % iron oxide, and up to 0.1 wt. % vitamin premix. The mixture is mixed in a double ribbon mixer and compressively shaped into blocks. The feed supplement is distinguishable for requiring at least 20 wt. % magnesium oxide.

U.S. Pat. No. 1,645,703 issued on Oct. 18, 1927, to William H. Lapp describes a supplemental poultry food composition comprising 50–51% calcium carbonate, 14% bone and meat meal, 12% bone meal, 5% vegetable charcoal, 4% ferrous sulfate, 4% sulfur, and 10% sodium chloride. The poultry food composition is distinguishable for containing ferrous sulfate and sulfur, but lacking potassium.

U.S. Pat. No. 4,452,779 issued on Jun. 5, 1984, to Vernon L. Cockerill describes a method and composition for increasing the milk quality of sows and gilts comprising 65 wt. % sodium sulfate, 13 wt. % magnesium sulfate, 12 wt. % sulfur, and 10 wt. % anhydrous sodium sulfate. The composition is added to a complete feed in the amount of at least 0.5 wt. % to maintain the electrolyte balance. The feed composition is distinguishable in lacking the greater quantity added in the present invention and the requirement for magnesium sulfate.

U.S. Pat. No. 2,504,664 issued on Apr. 18, 1950, to Walter Baker describes a feed formula for chickens and domestic animals that depend mainly on a grain and mineral mixture. The poultry feed contains calcium, phosphorus, yeast, iodine, mash material, and mineral oil. Potassium iodide is added in the amount of 0.093 to 0.125 pound per ton of the poultry feed mixture.

U.S. Pat. No. 2,683,664 issued on Jul. 13, 1954, to Alvis E. Greer describes a mineral concentrate as a dietary supplement for animals and poultry comprising the formation of a trace mineral premixture-containing 76.1 wt. % defluorinated calcium phosphate, 10 wt. % manganese carbonate, 5.8 wt. % zinc carbonate, 4.55 wt. % copper carbonate, and 2.8 wt. % potassium iodide. The final mineral concentrate was formed by adding 1 wt. % of the trace mineral premixture to 50 wt. % sodium chloride, 35 wt. % defluorinated calcium phosphate, and 5 wt. % each of calcium carbonate and potassium sulfate. The mineral concentrate composition is distinguishable for its 50 wt. % sodium chloride 35 wt. % calcium phosphate.

U.S. Pat. No. 4,182,755 issued on Jan. 8, 1980, to Larry C. McNeff describes a feed composition and method for feeding poultry and domestic animals which include a chloride ion intake control agent comprising calcium chloride, ammonium chloride, aluminum chloride, ferric chloride, magnesium chloride, and mixtures thereof. The control agent for swine is added to 60 to 90 wt. % grain products and 7.5 Wt. % plant products, and minor amounts of protein, molasses, vitamins, and minerals containing 0.35–6.0 wt. % sodium chloride, calcium carbonate, and calcium phosphate. The control agent composition is distinguishable for requiring chlorides of ammonium, iron, aluminum, and magnesium.

U.S. Pat. No. 4,540,577 issued on Sep. 10, 1985, to Richard B. Hunt et al. describes a nutritional mineral supplement for animal feeds made by mixing 5–6 wt. % amorphous sulfur, 8–12 wt. % potassium chloride, and 82–87 wt. % langbeinite when prepared by mixing the ingredients, heating to 110–115° C., adding amorphous sulfur with agitation, and cooling. 3–40 lb. of supplement mixture was added to a ton of animal feed. The mineral supplement composition is distinguishable for requiring sulfur.

U.S. Pat. No. 4,560,561 issued on Dec. 24, 1985, to Charles J. Henderson et al. describes a method of preparing a poultry feed supplement composition and the composition for hardening the egg shells by agglomerating a waste lime (calcium carbonate) from a sugar refining process with less than 20 wt. % of beet molasses, cane molasses, wood molasses, citrus molasses, corn steep liquor, invert sugar solution, and mixtures thereof, adjusting the moisture content to 18–23 wt. %, formed into 1/16 inch diameter pellets, dried to a moisture content up to 4 wt. %. The poultry feed supplement composition is distinguishable for utilizing lime and various molasses.

U.S. Pat. No. 4,857,332 issued on Aug. 15, 1989, to Brian R. Schricker describes a pelleted composition and method for increasing milk fat in ruminants comprising a sodium or magnesium antacid and an electrolyte selected from the group consisting of potassium, sodium, and chlorine containing electrolytes. The pellets contain 1.5–1.8 parts of potassium and 1.2–1.5 parts chlorine per part of sodium. The potassium must be present in amount to provide 0.8–1 wt. parts per weight part of any magnesium and sodium bicarbonate. Sodium sesquicarbonate and trona can be substituted for sodium bicarbonate. The composition is distinguishable for requiring sodium bicarbonate and magnesium oxide for only ruminants.

U.S. Pat. No. 4,976,963 issued on Dec. 11, 1990, to Brian R. Schricker et al. describes a ruminant and human feed antacid composition containing potassium, sodium and chlorine in the form of magnesium oxide, sodium bicarbonate, dolomite, sodium hydroxide, calcium hydroxide, calcium carbonate, magnesium carbonate, sodium carbonate, northupite, and mixtures thereof. Electrolyte sources are potassium chloride, langbeinite, potassium bicarbonate, arcanite, potassium hydroxide, potassium phosphates, potassium carbonate, sodium chloride, and mixtures thereof. The weight ratio among elements must be within 10% of 1.65:1:1.35:1.88 of potassium:sodium:chlorine:magnesium. Magnesium is not required. The materials must be ground to 48 to 8 Tyler mesh before agglomerating into pellets. 2 to 5 wt. % bentonite, starch, hydraulic cement or clay binders are required to resist breakage. The compositions are distinguished for adding minerals, phosphates, sodium hydroxide, and magnesium.

U.S. Pat. No. 5,252,346 issued on Oct. 12, 1993, to Vernon E. Krause describes a method for preparing a stable thixotropic animal feed suspension supplement consisting of mixing a sugar solution with 5–14 wt. % starch containing a feed stuff ingredient selected from wheat, corn, milo, and mixtures thereof, and subsequently adding 20–25 wt. % calcium carbonate. The feed composition is distinguishable for containing only starch and calcium carbonate.

U.S. Pat. No. 5,976,580 issued on Nov. 2, 1999, to Francis J. Ivey et al. describes a high moisture nutrient composition for poultry and other birds containing at least 50 wt. % water, at least 10 wt. % digestible carbohydrate, and optionally bile salts, surfactants, enzymes, hormones, protoglandins, peptides, immunoglobulins, cytokines, vaccines, antioxidants, amino acids, antibiotics, vitamins, and minerals. The composition for feeding poultry is distinguishable for lacking electrolytes.

U.S. Pat. No. 6,261,609 B1 issued on Jul. 17, 2001, to Thomas G. Cates, II describes a range feed supplement in granular form for ruminants having about 27–33 wt. % sodium chloride, about 20 wt. % phosphate, about 5–25 wt. % sodium bicarbonate and sesquicarbonate, about 4 wt. % magnesium oxide, about 10 wt. % potassium chloride, about 10 wt. % sulfur, and cane molasses. The composition is distinguishable for requiring phosphates, sulfur and magnesium oxide.

U.K. Patent Application No. 280,774 published on Nov. 24, 1927, for Rowland Jones describes a feed composition for feeding poultry and livestock comprising pellets of oatmeal, dried yeast, maize meal, bran, middlings, oats, alfalfa meal, fish meal, and cod liver oil. The composition varies for day-old chicks, growers stage poultry, winter laying hens, and breeding hens. The feed compositions are distinguishable for emphasizing the ratio of albuminoids to carbohydrates and fats.

U.K. Patent Application No. 711,349 published on Jun. 30, 1954, for Eric H. Broadfoot describes foodstuffs for cattle, pigs and poultry to prevent disease comprising 1–10 lbs. sodium bicarbonate, disodium hydrogen phosphate or sodium lactate; 1–10 lbs. calcium phosphate powder; 20–60 lbs. molasses; 10 lbs. seaweed; and 1 cwt. forage meal. The composition is distinguishable in the absence of sodium chloride and the addition of phosphates.

U.K. Patent Application No. 1,330,209 published on Sep. 12, 1973, for Ivar H. Sanick describes a supplementary feed for development of chicken meat in broiler meat comprising 5 kg. minced and dried (medicago sativa) Lucern with crushed corn, wheat bran, crushed oats, skim milk powder, dried meat scraps, bone meal, salt, cod liver oil, fish meal, and minced and dried allium sativum. The feed composition is distinguishable for requiring Lucern.

U.K. Patent Application No. 2 266 652 A published on Nov. 10, 1993, for Young K. Yeo describes a feed composition for broiler chickens comprising 40–70 wt. % n-3 fatty acid (linseed, perilla seed, fish meal), 25–50 wt. % carbohydrate (wheat or barley), 2–4 wt. % fiber (alfalfa), 0.3–0.6 wt. % antioxidant (santoquin), 0.3 wt. % salt, and 0.7 wt. % dicalcium phosphate. The feed composition is distinguishable for requiring a predominant amount of linseed, perilla seed and fish meal.

Canada Patent Application No. 1,328,371 published on Apr. 4, 1994, for J. Wallace Sawhill describes an animal feed supplement with filler comprising molasses of calcium hydroxide or calcium oxide, sulfuric acid or phosphoric acid, a protein meal, and filler containing hulls, shells of grains and nuts. Magnesium oxide or hydroxide can be added. The supplement feed composition is distinguishable for requiring acids.

European Patent Application No. 0 616 777 A2 published on Sep. 28, 1994, for Yasuo Katta et al. describes a domestic fowl feed additive composition containing a galacto-oligo-saccharide prepared by heat-treating lactose in mineral acid. The feed additive is added to corn or milo, vegetable oil meal, fish meal, corn gluten or rice bran, calcium carbonate and sodium chloride, and vitamins. The feed additive composition is distinguished for requiring the acid treated lactose.

Canada Patent Application No. 2,269,397 published on Oct. 24, 1999, for Tetsuo Yamane et al. describes a nutrition enriched composition for animals (chickens) and marine animals (flatfish) comprising soybean oil substituted for fish meal. The bodies of fish, krill and cuttlefish are finely ground and mixed with a proteolytic enzyme and reacted at 30–60° C. for 1 to 2 hours. The enzyme is inactivated by heating to 80–100° C. and 0.1–10 wt. % mixed with feed containing 60% corn, 22% soybean oil meal, 7% wheat bran, and 8% corn gluten meal, vitamins, minerals, etc. for chickens. The feed supplement composition is distinguished for requiring a proteolytic enzyme treated fish meal ingredient.

None of the above inventions and patents, taken either singularly or in combination, is seen to describe the instant invention as claimed. Thus, a poultry and livestock feed additive solving the aforementioned electrolyte balance problems is desired.

SUMMARY OF THE INVENTION

The present invention is an animal feed additive containing an appropriate dietary electrolyte balanced composition comprising potassium sulfate, sodium sesquicarbonate, potassium chloride, potassium carbonate, calcium carbonate, sodium bicarbonate, sodium sesquicarbonate, roughage products such as either a rice mill by-product, soybean hulls or peanut hulls, and mineral oil. The animal feed additive contains 36% by weight electrolytes based on 23.45% to 25% potassium and 11.7% to 14% sodium. One to four pounds of the electrolyte composition is added to a ton of avian feed or a ratio range of 0.0005 to 0.002 for a pound of avian feed. For other farm species such as livestock, the electrolytes are used at levels to balance their standardized dietary electrolyte balance. The electrolytes have been found to improve the breeder hen performance as related to egg production, body weight, and reduced mortality from heat stress. Inclusion of the electrolytes in chicken feed increases the processing yield, feed conversion, and body weight of broilers which are young chickens up to 2.5 pounds in dressed weight. Turkeys benefit substantially as chickens from the addition of proper amounts of electrolytes to their feed.

Accordingly, it is a principal object of the invention to provide a poultry and livestock feed additive containing electrolytes with roughage products and mineral oil.

It is another object of the invention to provide a poultry and livestock feed additive containing the proper amount of electrolytes for each species based on their electrolyte level.

It is a further object of the invention to provide a balanced poultry feed additive containing 36 wt. % electrolytes.

Still another object of the invention is to provide a balanced poultry feed additive containing electrolytes such as sulfates, chlorides, carbonates, bicarbonates, and sesquicarbonates of sodium, potassium and calcium.

It is an object of the invention to provide an improved poultry and livestock feed additive for the purposes described which is inexpensive, dependable and fully effective in accomplishing its intended purposes.

These and other objects of the present invention will become readily apparent upon further review of the following specification.

DETAILED DESCRIPTION OF THE PREFERRED EMBODIMENTS

The present invention is directed to a poultry and livestock feed formula for increased production. However, background information regarding the role of electrolytes in animal nutrition should be understood.

Electrolytes are defined as the compounds that dissolve into positive (cation) and negative (anion) entities in an animal body solution and have the inherent ability to conduct an electric current. The three chemical ionic elements that are predominant in satisfying the electrolytic balance within a living body are sodium, potassium and chloride. All classes of livestock have definite nutrient requirements for these elements in the correct amounts for body homeostasis known as a dietary electrolyte balance. All essential nutrients such as the amino acids, vitamins, minerals, and oxygen must be continually supplied to maintain the well-being of production livestock, increase growth and foster reproduction. Similarly, sodium and potassium as minerals must be continuously supplied to obtain the desired production goals with all types of livestock.

While sodium is the fifth most abundant mineral found in the body, potassium ranks third behind calcium and phosphorus. In the past 30 to 40 years, the increased role and requirement of potassium has received little attention from researchers. Since potassium is the principal cation of intracellular fluid, its concentration is very high in red corpuscles, nerves and muscle tissue. Many nutrients are able to maintain body reserves, but potassium cannot sustain an adequate reserve, especially during periods of stress and high temperature.

Potassium is the primary intracellular cation associated with maintaining the acid-base and osmotic balance between body fluids and cells. Potassium is prominent in cardiac muscle activity. Other body functions of potassium comprise enzyme activation, oxygen and carbon dioxide transport, water balance, and nerve and muscle excitability. Potassium is important for optimal nitrogen retention. The reported requirement for potassium in relationship to nitrogen retention is 5 milli-equivalents (mEq) for each gram of amino acid nitrogen for optimal retention.

With present intense animal production, in terms of growth rate, feed conversion and congested production units, livestock producers are facing two completely different types of stress. Heat is the most recognized stress factor, but the effect of the heat factor is governed by climatic conditions and the ability of the producer to cool the birds and animals.

All warm-blooded animals including humans may be subjected to three zones of thermal comfort. The ideal zone is known as the thermoneutral zone where the body expends no energy to cool or heat itself. To a point below or above the thermoneutral zone, the body must employ energy to heat or cool, respectively, until a critical temperature is reached, at which point the organism cannot survive. Competitive confinement stress is the permanent stress that is automatically induced by high-density confinement rearing. This stress will be encountered in most phases of swine and poultry production and in cattle feedlots.

Animals, especially poultry, have little ability to conserve body stores of potassium. During heat stress, water balance and potassium deficiencies are often experienced. Poultry dissipate heat by panting or evaporative cooling. Many producers use vitamin-electrolyte water soluble materials to alleviate heat stress as a hit or miss solution to this problem. Electrolytes should be constantly provided for poultry and live-stock to protect against all types of stress, both thermal and confinement.

Most of the research done on the requirements of potassium was conducted during a twenty year span from the 1950's. The potassium requirement for broiler chickens was determined in the late 1950's using a bird that performs less than half the capacity of today's bird in terms of growth rate. In the early 1960's, it took a producer eight weeks to produce a 3.2 to 3.4 pound broiler chicken with a feed conversion from 2.2 to 2.25. Today, a 6.5 pound bird can be produced in eight weeks with a feed conversion of 2.18, whereas a 3.9 pound bird can be produced in 40–41 days with a feed conversion of 1.88. It takes 2 to 3% less feed to produce 18% more meat in 29% less time with the genetically improved broiler chicken used for current meat production. Additionally, the potassium availability from natural foodstuffs may be as low as 73% leading to borderline conditions in certain rations during times of stress or for maximum processing of chicken breast meat.

The electrolyte balance in commercial chicken layers and chicken broiler breeders has been shown to have a substantial effect on shell quality and egg production. Shell formation within the bird creates an acidosis condition from the formation of hydrogen ions generated during calcium carbonate synthesis. Correct electrolyte balance in the chicken layer is necessary to alleviate this condition. Water balance is also important during times of extreme heat stress both in broiler breeders and caged commercial layers.

Many poultry diets are marginal in potassium, especially if animal protein comprises a large percentage of the protein content. Ionophore coccidiostats also have a profound influence on electrolyte demand from the diet.

While the concern for electrolyte concentration within the diet is extremely important, of equal importance is the dietary electrolyte balance. The electrolyte balance is defined as the Na+K−Cl in milliequivalents (mEq/Kgm) of diet. It is notably significant that the balance of these three chemical elements be within their acceptable ranges, and that none be excessive or deficient within the diet.

In contrast to potassium, sodium is the major cation in extracellular fluid and is closely associated with chloride anion and bicarbonate anion in the management of acid-base balance. Sodium functions in the maintenance of osmotic pressure of body fluid and the protection against excessive body fluid loss. The permeability of cells and the sustaining of normal muscle irritability are additional functions of sodium. Sodium is also required for absorption of amino acids and sugars in the small intestine. Therefore, utilization of digested protein and carbohydrates is diminished with sodium deficiency. Similarly, both sodium and chloride ions aid in nutrient passage and waste removal in cell nourishment and maintenance. While sodium is seldom deficient in the diet, a deficiency of sodium will cause growth reduction, increased feed conversion, gonadal deficiency, bone-softening, corneal keratinization, decreased cellular volume, and changes in cellular function. Current nutritional levels of dietary sodium range from 0.18 wt. % to 0.25 wt. % for poultry.

The dietary electrolyte requirements for turkeys were assessed twenty to forty years ago. The industry is dealing with a vastly improved bird in terms of growth rate, feed conversion, and yield potential. The dietary potassium requirement of turkeys is directly correlated with its growth rate potential.

Commercially grown hens are constantly subjected to confinement stress and to heat stress during environmental periods. Feed consumption may be severely restricted during hot weather initiating a decrease in egg production and egg size which may be related to sodium deficiency. Dietary potassium deficiency will result in reduced production, egg weight, shell thickness, and albumin content. An extreme severe deficiency will result in weakness, inability to stand and death of the bird. "Cage layer fatigue" is associated with electrolyte imbalance.

Supplemental electrolytes should be added to a broiler stage chicken's intake to boost body levels because of increased excretion during stress and hot weather. The supplementation of potassium is particularly critical at this time. A reduction in plasma potassium has been positively correlated with increased bird mortality during heat stress. A 9% increase in weight gain, a 40% increase in water consumption and a lowering of body temperature was demonstrated with broiler chickens receiving electrolyte supplementation.

An increase in hen-housed breeder mortality has occurred since the introduction of the meat-type broiler chicken. It is becoming apparent that early protein and critical electrolyte balance are critical factors to be considered in improving breeder hen performance as related to egg production and mortality. Ricket-like conditions and severe electrolyte imbalances, especially potassium, are contributing factors seen in the early weeks of sexual maturity. This fact may be due to the stress of the onset of sexual maturity in a hen that is not physiologically prepared to deal with the predicament. Certainly, there is insufficient research to ascertain the nutrient requirements of the pullets and breeders of the meat strains, and adjustments will be forthcoming to dietary requirements of these breeds.

It has been shown that the sodium-chloride-potassium concentration should range between 200 to 300 mEq/kgm for optimal growth rate in broiler chickens. Turkey breast yield of tom turkeys was shown to be increased using an electrolyte balance from 150–250 mEq/kgm. Another report suggested an electrolyte balance of 250 mEq/kgm for tom turkeys. The present invention recommends the following usage levels in the table for the electrolyte feed composition for cool and warm or hot weather.

TABLE

| FEED TYPE | POUNDS/TON FEED | |
| --- | --- | --- |
| | COOL | WARM/HOT |
| BROILERS: | | |
| Broiler starter | 1.0–1.2 | 1.0–1.5 |
| Broiler grower | 1.2–1.5 | 1.5–2.0 |
| Broiler finisher | 2.0–2.2 | 2.2–2.5 |
| Broiler withdrawal | 2.2–2.5 | 2.5–3.0 |
| BREEDER PULLETS AND BREEDER LAYERS: | | |
| PULLET STARTER | 1.5–2.0 | 1.5–2.0 |
| PULLET GROWER | 1.0–1.5 | 1,0–2,0 |
| PULLET DEVELOPER | 1.0–1.5 | 1.0–2.0 |
| PRE-LAYER | 1.5–2.0 | 2.0–2.5 |
| BREEDER I | 2.0–2.2 | 2.0–2.5 |
| BREEDER II | 2.0–2.2 | 2.0–2.5 |
| MALE FEED | 2.0–2.5 | 2.0–2.5 |
| COMMERCIAL LAYERS: | | |
| PULLET FEEDS | 1.0–1.5 | 1.0–2.0 |
| LAYER FEEDS | 1.5–2.0 | 1.5–2.5 |
| TURKEYS: | | |
| MEAT TURKEY FEEDS | 1.0–4.0 | 1.0–4.0 |
| TURKEY BREEDER FEEDS | 1.0–3.0 | 1.0–3.0 |

The preferred poultry and livestock feed additive in powder form comprises 30–40 wt. % of a dietary electrolyte selected from mixtures of sodium, potassium and calcium in the form of carbonates, sulfates and chlorides; 55–60 wt. % of a roughage product selected from the group consisting of a rice mill by-product, soybean hulls and peanut hulls; and 0.001–0.010 wt. % mineral oil to form a powdered product.

The dietary electrolyte feed contains calcium carbonate, potassium sulfate, potassium carbonate, potassium chloride, and sodium sesquicarbonate in certain proportions. The dietary electrolyte feed contains a predominant amount of potassium chloride and sodium sesquicarbonate. Preferably, the dietary electrolyte has a predominant amount of potassium chloride and sodium sesquicarbonate and the balance includes calcium carbonate and potassium sulfate. The potassium chloride and sodium sesquicarbonate are present in substantially equal amounts. The preferred amount of dietary electrolyte in the feed additive is 36 wt. % with potassium in the range of 23.45 wt. % to 25 wt. % and sodium in the range of 11.7 wt. % to 14 wt. %

The poultry and livestock feed additive composition is formed in powder form which can be placed in 50 lb. bags for distribution. The preferred amount of feed additive for poultry is 1 to 4 pounds per ton of complete diet.

The method of preparing and feeding poultry and livestock a feed additive containing an appropriate amount of electrolytes comprises a first step of grinding a mixture of organic roughage product selected from the group consisting of a rice mill by-product, soybean hulls and peanut hulls. The rice mill by-product is preferred. The next step involves the mixing of the ground mixture of organic roughage product with mineral oil in a ribbon blender apparatus. Then, a dietary electrolyte mixture selected from mixtures of sodium, potassium and calcium in the form of carbonates, sulfates and chlorides given above and in the proportions given is added to mixing material to form a powdered product containing an appropriate amount of electrolytes for feeding poultry and livestock.

It is to be understood that the present invention is not limited to the embodiments described above, but encompasses any and all embodiments within the scope of the following claims.

I claim:

1. An animal feed additive for maintaining electrolytic balance in poultry and livestock, said additive comprising:
   - 30–40% by weight of a dietary electrolyte mixture, said mixture comprising potassium sulfate, potassium chloride, potassium carbonate, calcium carbonate, sodium bicarbonate and sodium sesquicarbonate;
   - 55%–60% by weight of an organic roughage product, said roughage product being selected from the group consisting of a rice mill by-product, soybean hulls, and peanut hulls; and
   - 0.001%–0.010% by weight of mineral oil;

wherein said additive is formulated as a powder.

2. The feed additive of claim 1, comprising about 36% by weight of said electrolyte mixture.

3. The feed additive of claim 1, wherein said electrolyte mixture comprises about 23% to about 25% by weight of potassium.

4. The feed additive of claim 1, wherein said electrolyte mixture comprises about 11% to about 14% by weight of sodium.

* * * * *